United States Patent [19]

Delaunay

[11] Patent Number: 5,178,763
[45] Date of Patent: Jan. 12, 1993

[54] METHOD AND APPARATUS FOR PREPARING A SUBSTITUTION LIQUID

[75] Inventor: Marc Delaunay, Decines, France

[73] Assignee: Hospal Industrie, Meyzieu Cedex, France

[21] Appl. No.: 683,555

[22] Filed: Apr. 10, 1991

[30] Foreign Application Priority Data

Apr. 13, 1990 [FR] France ................................ 90 05034

[51] Int. Cl.⁵ .............................................. B01D 61/00
[52] U.S. Cl. .................................... 210/644; 210/181; 210/205; 210/209; 210/321.64; 210/321.71; 210/321.72; 210/639; 210/641; 210/645; 210/646; 210/647; 210/742
[58] Field of Search .............. 210/639, 641, 644, 645, 210/646, 647, 742, 181, 205, 206, 209, 257.2, 321.64, 321.71, 321.72–321.81

[56] References Cited

U.S. PATENT DOCUMENTS

| | | | |
|---|---|---|---|
| 3,598,727 | 8/1971 | Willock | 210/321.71 |
| 3,839,200 | 10/1974 | Gigou et al. | 210/321.72 |
| 4,702,829 | 10/1987 | Polaschegg et al. | 210/195.2 |
| 4,889,635 | 12/1989 | Chevallet | 210/646 |
| 4,894,164 | 1/1990 | Polaschegg | 210/742 |
| 4,950,395 | 8/1990 | Richalley | 210/321.71 |
| 4,968,432 | 11/1990 | Antwiler | 210/321.72 |
| 5,024,756 | 6/1991 | Sternby | 210/647 |
| 5,092,836 | 3/1992 | Polaschegg | 210/646 |

FOREIGN PATENT DOCUMENTS

| | | |
|---|---|---|
| 0097863A3 | 1/1984 | European Pat. Off. |
| 0228781A1 | 7/1987 | European Pat. Off. |
| 0276376A3 | 8/1988 | European Pat. Off. |
| 2025787 | 1/1980 | United Kingdom ........ 210/647 |

Primary Examiner—Robert A. Dawson
Assistant Examiner—Sun U. Kim
Attorney, Agent, or Firm—Finnegan, Henderson, Farabow, Garrett & Dunner

[57] ABSTRACT

The invention is directed to an apparatus and method for transforming a sterile pyrogen-free liquid into a substitution liquid using an exchanger. The method includes the steps of flowing first and second liquids over opposite sides of a semipermeable membrane, the first liquid being sterile and pyrogen-free. Both liquids contain at least some electrolytes of blood including at least a buffer agent or a precursor of a buffer agent. At least some of the electrolytes have different concentrations in the two liquids. When purifying blood by hemodiafiltration, this method has the particular advantage that, rather than discarding the second liquid, it can be used for hemodiafiltration.

21 Claims, 2 Drawing Sheets

METHOD AND APPARATUS FOR PREPARING A SUBSTITUTION LIQUID

BACKGROUND OF THE INVENTION

1. Field of the Invention

The present invention relates to a method and to apparatus for preparing a substitution liquid.

2. Description of the Related Art

The term "substitution liquid" is used to designate a liquid for injection into the vascular circuit of a patient suffering, for example, from severe burns or having lost large quantities of blood or else a patient subject to blood purification treatment by hemofiltration or by hemodiafiltration, prescribed after temporary or permanent loss of renal function.

The invention is particularly applicable to treatment of this type since the quantity of substitution liquid required during a hemofiltration or a hemodiafiltration session may be very large (with some patients, as much as 30 liters for a four-hour session).

A substitution liquid must be sterile and pyrogen-free, i.e. it must be free from any pathogen and from any substance that could give rise to a febrile reaction in the patient. In addition, it must be isotonic relative to blood, i.e. it must have the same electrolytic concentration as blood. The relative proportions of cations and anions resulting from the dissociation of the electrolytes in the substitution liquid are adjusted as a function of patient requirements, depending on whether the patient's electrolytic equilibrium needs to be maintained or to be re-established.

Finally, a substitution liquid must contain at least those blood electrolytes which play an essential role in the metabolism, i.e., when dissociated in the form of cations and anions: sodium, potassium, calcium, and magnesium as cations, and chlorides and bicarbonates as anions, with the bicarbonates being essential to perform the buffer agent function.

The characteristics of a substitution liquid as recalled above, namely its sterility, its pyrogen-free nature, its isotonia relative to blood, and its specific electrolytic composition, mean that preparing a substitution liquid is difficult and requires special precautions.

In hospitals, it is common practice to use substitution liquids of standard composition prepared industrially by specialized suppliers. These liquids suffer from the drawback of being expensive. In addition, when they contain bicarbonates, they present storage difficulties that are not fully resolved at present, due to a combination of two factors. The first of these factors is that bicarbonates are unstable and decompose spontaneously and continuously into carbon dioxide when they are not confined in gastight manner. The second of these factors is that the bags used for packaging the substitution liquids are generally gas permeable. As a result, if it is desirable to use a substitution liquid having a precise concentration of bicarbonate, then the liquid must be used very soon after it has been packaged, and this constitutes a constraint on the user.

U.S. Pat. No. 4,702,829 describes apparatus for preparing a substitution liquid specifically for use during hemodiafiltration treatment, which apparatus mitigates these drawbacks in part. In that patent, proposals are made to prepare a substitution liquid on the basis of a dialysis liquid manufactured in a dialysis liquid generator, with dialysis liquids generally having substantially the same composition as standard substitution liquids but being neither sterile nor pyrogen-free. The apparatus described in that patent comprises a branch on the dialysis circuit, which branch includes two sterile filters between which a circulation pump is disposed.

In addition to being unsuitable for responding to a very specific requirement, that apparatus suffers from the drawbacks inherent to using expensive filters that must be changed regularly and whose possible clogging must always be detected in time.

SUMMARY OF THE INVENTION

An object of the present invention is to provide a method for preparing a substitution liquid which is not specific to a particular treatment, which is simple, and which is relatively cheap to implement.

Another object of the invention is to provide apparatus enabling the method to be implemented.

Another object of the invention is to provide such apparatus which is particularly adapted to treatment by hemodiafiltration.

According to the invention, these objects are achieved by a method for preparing a substitution liquid, the method being characterized in that it consists in causing a sterile and pyrogen-free first liquid and a second liquid to flow over opposite sides of a semipermeable membrane in an exchanger, said liquids containing at least some of the electrolytes of blood including at least one buffer agent or at least one precursor of a buffer agent, at least some of the electrolytes being at different concentrations in the two liquids upstream from the exchanger, the substitution liquid being constituted by the first liquid downstream from the exchanger.

This method has the advantage of enabling a first sterile and pyrogen-free liquid to be enriched with determined electrolytes in determined proportions and without risk of contamination by means of a second liquid that need be neither sterile nor pyrogen-free, with the first liquid advantageously being selected from standard solutions having simple electrolytic composition which are readily available and cheap.

According to a characteristic of the invention, the second liquid is used downstream from the exchanger as a dialysis liquid.

This disposition is particularly advantageous in hemodiafiltration treatment since it enables a substitution liquid and a dialysis liquid to be prepared simultaneously using common preparation means.

According to another characteristic of the invention, one of the liquids is heated upstream from the exchanger so that downstream from the exchanger the first liquid has a temperature which is close to that of the human body.

When the heated liquid is the second liquid, then the exchanger, which is provided primarily for ion transfer, is also used as a heat exchanger. This disposition is particularly advantageous when the source of the second liquid is a dialysis liquid generator, since such generators usually include means for heating the liquid.

The present invention also provides an apparatus for preparing a substitution liquid, the apparatus being characterized in that it comprises an exchanger comprising two chambers separated by a semipermeable membrane, a first chamber having an inlet connected to a source of a first liquid which is sterile and pyrogen-free, and an outlet for connection to a receptacle (a patient or a supply of extemporaneous liquid), a second chamber having an inlet connected to a source of a second liquid, and an outlet for optional connection to a dialyzer, said liquids containing at least some of the electrolytes of blood and including at least one buffer agent or precursor for a buffer agent, at least some of the electrolytes being at different concentrations in the two liquids upstream from the exchanger.

BRIEF DESCRIPTION OF THE DRAWINGS

Other characteristics and advantages of the invention appear from reading the following description made with reference to the accompanying drawings, in which.

DESCRIPTION OF THE PREFERRED EMBODIMENTS

Figure 1:
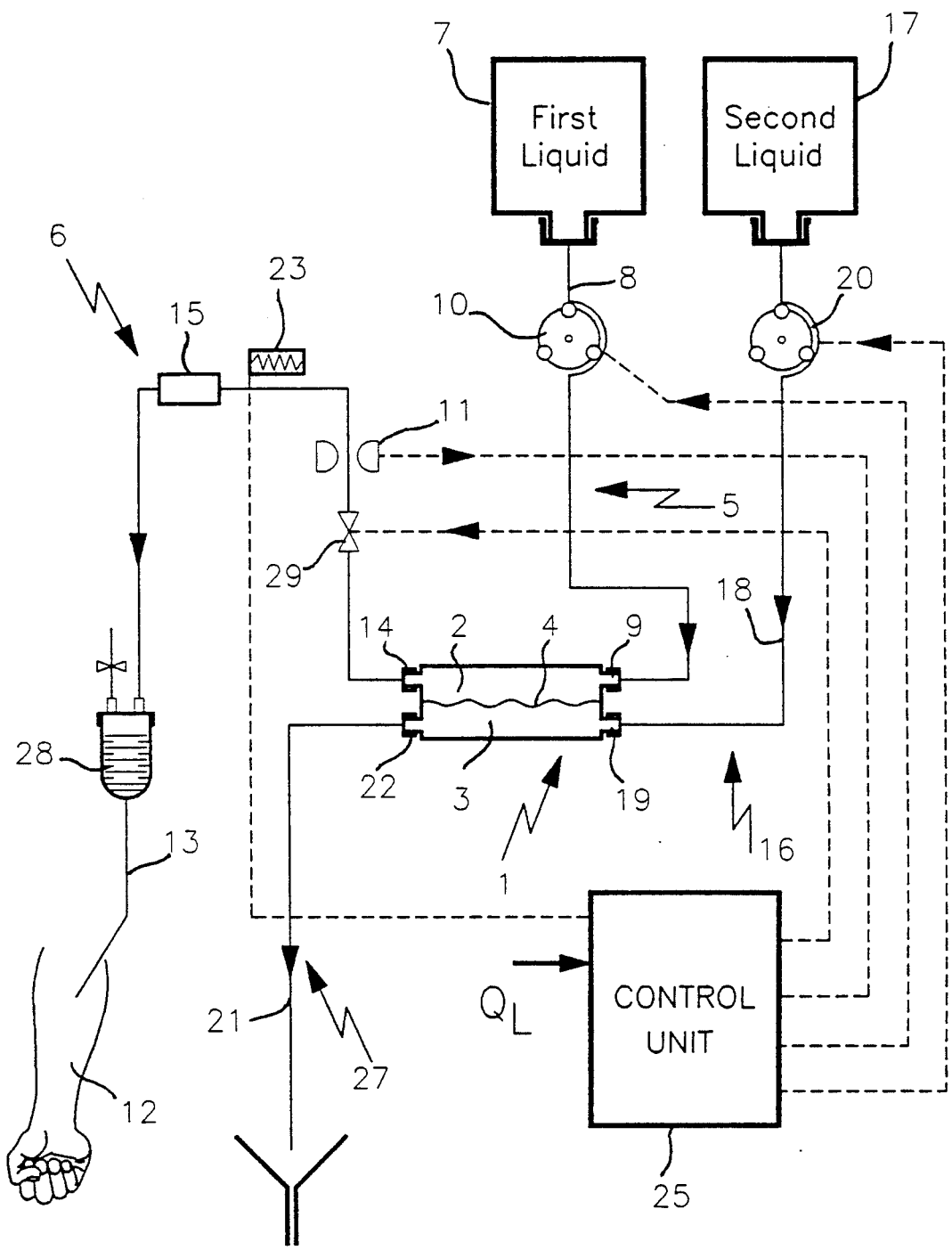
FIG. 1 is a diagram of apparatus of the invention for preparing a substitution liquid.

The apparatus shown in FIG. 1 for preparing substitution liquid comprises an exchanger 1 having first and second chambers 2 and 3 separated by a semipermeable membrane 4 and connected to a first circuit and to a second circuit for conveying respective flows of liquids whose natures are specified below.

The first circuit comprises two portions 5 and 6 situated respectively upstream and downstream from the exchanger 1 relative to the liquid flow direction through said first circuit. The upstream portion 5 of the first circuit comprises a supply 7 for a first liquid connected via a duct 8 to an inlet 9 of the first chamber 2 of the exchanger 1. A peristaltic pump 10 is disposed on this portion of the first circuit to cause the first liquid to flow from the supply 7 towards the exchanger 1, and to adjust its flow rate. A flow meter 11 is disposed downstream from the exchanger 1 for accurately measuring the flow rate of the liquid injected into a patient 12.

In a simplified variant of the apparatus of the invention, the first circuit does not include the pump 10, nor does it include a flow meter 11. Rather the flow of the first liquid is driven by gravity, due to the supply 7 being placed higher than the patient 12. The duct 8 is then provided with a valve for adjusting the flow rate of the first liquid.

The downstream portion 6 of the first circuit includes a duct 13 having one end connected to an outlet 14 of the first chamber 2 of the exchanger 1 and having a cannula at its other end for insertion into a vein of the patient 12. Where applicable, this second end may also be connected to an extemporaneous supply of substitution liquid. The duct 13 passes through a degassing chamber 28. As a safety measure, an antibacterial filter 15 may be placed in the duct 13 upstream from the degassing chamber 28.

A heater member 23 is disposed in the downstream portion 6 of the first circuit to raise the liquid injected into the patient 12 to a temperature close to 37° C. when the flow rate of this liquid is greater than about 1 liter/hour (beneath this flow rate, it is acceptable to inject a patient with liquid at ambient temperature).

The second circuit also comprises two portions 16 and 27 respectively situated upstream and downstream from the exchanger 1 relative to the direction of liquid flow in said second circuit. The upstream portion 16 of the second circuit comprises a supply 17 for a second liquid, connected via a duct 18 to an inlet 19 of the second chamber 3 of the exchanger 1. A peristaltic pump 20 is disposed on this second portion of the circuit to cause the second liquid to flow from the supply 17 towards the exchanger 1, and to adjust its flow rate.

In a simplified variant of the apparatus of the invention, no pump is provided in the upstream portion 16 of the second circuit and the second liquid is caused to flow under gravity, with the supply 17 being placed higher than the patient 12. The duct 18 is then provided with a valve to adjust the flow rate of the second liquid.

In a variant apparatus of the invention, the heater member 23 is no longer disposed in the downstream portion 6 of the first circuit, but in the upstream portion 16 of the second circuit, with the first liquid then being heated by the second liquid in the exchanger 1.

The downstream portion 27 of the second circuit includes a duct 21 having one end connected to an outlet 22 of the second chamber 3 of the exchanger 1, and having its other end opening out into a wastewater drain circuit.

As can be seen in FIG. 1, the upstream portions 5 and 16 and the downstream portions 6 and 27 of the first and second circuits are connected to the exchanger 1 so that the first and second liquids flow therethrough in the same direction. This disposition, which is not the most favorable disposition for interchange between the two liquids (which interchange is specified below), nevertheless has the advantage of the hydraulic pressure gradients on either side of the membrane having the same sign. As a result, even if the membrane 4 of the exchanger 1 is a high permeability membrane, the risk of the second liquid ultrafiltering into the first circuit is small.

To eliminate this risk, which is unacceptable given that the first liquid must not be polluted under any circumstances, a head loss device 29 is placed in the first circuit downstream from the exchanger 1 so as to maintain a permanent positive transmembrane pressure between the chamber 2 and the chamber 3 in the exchanger 1. This head loss device may be adjustable and may be controlled by a control unit 25 to maintain the transmembrane pressure substantially constant, with control being as a function of the pressures that exist in the first and second circuits respectively inside the exchanger 1.

The control unit 25 also serves to control the pump 10 as a function of a substitution liquid flow rate QL determined by the clinician and as a function of the measured flow rate of the first liquid as provided by the flow meter 11, with control ensuring that the flow rate of the substitution liquid actually injected into the patient 12 is substantially equal to QL, in spite of any ultrafiltration which may take place inside the exchanger 1 (which depends on the nature of the membrane 4). The control unit 25 also adjusts the amount of heating produced by the heater unit 23 as a function of the flow rate of the substitution liquid. Under certain conditions of use of this first apparatus, defined relative to the ratio of the flow rates through the exchanger 1 and by the characteristics of the exchanger 1 (nature and area of the membrane 4), it may also be advantageous to provide for the control unit 25 to adjust the flow rate of the pump 20 as a function of the flow rate of the pump 10, for example if the ion transfers inside the exchanger 1 are to be controlled accurately, as described below.

The operation of the apparatus described above is based on the principle whereby two liquids containing electrolytes at different concentrations exchange ions when they are put into contact via a semipermeable membrane, with each type of ion migrating by diffusion through the membrane from the side of the membrane where ion concentration is higher towards the side of the membrane where ion concentration is lower, and the exchange of ions continues until concentrations on both sides of the membrane are in equilibrium.

It is important to observe that depending on the respective flow rates of the first and second liquids through the exchanger 1 and depending on the characteristics of the exchanger 1 (the nature and the area of its membrane 4), the rate of ion transfer inside the exchanger, whose uniformity guarantees that a substitution liquid is prepared having a determined electrolytic concentration, depends to a varying extent on the ratio of the flow rates through the exchanger. Given the range of flow rates QL that are usually prescribed, it will be advantageous, within the bounds of possibility, to select an exchanger 1 and a second liquid flow rate in such a manner that the ion transfer rate is not influenced by or is little influenced by any variation in the flow rate of the first liquid. If this cannot be done, then the pump 20 is servo-controlled to the pump 10 so that the ratio of their respective flow rates remains substantially constant, in accordance with the disposition mentioned above.

In accordance with the invention, the first liquid is a sterile and pyrogen-free solution which preferably has an electrolytic composition that is simple. The second liquid is a solution which need be neither sterile nor pyrogen-free, and its electrolytic composition is determined as a function of the electrolytic composition of the first liquid, of the flow rates of the liquids through the first and second circuits, and of the specific requirements of the patient 12, in such a manner that the substitution liquid per se, i.e. the liquid which flows in the downstream portion 6 of the first circuit, constituted by the first liquid enriched with ions and optionally heated by the second liquid, has an electrolytic composition, an ion concentration, and a temperature all appropriate to the patient. In principle, a standard composition is used for the first liquid, thereby making it easy to obtain on the market. The second liquid whose preparation does not require special precautions and is within the competence of ordinary pharmacy within hospitals, is advantageously the result of diluting concentrated saline solutions or salts in the solid state in distilled water.

By way of example, the following three pairs of liquids may be used in apparatus of the invention:

EXAMPLE 1

The first liquid is a solution of sodium chloride at a concentration substantially equal to that in blood. The second liquid contains the principal elecrolytes of blood, i.e., dissociated in the form of cations and anions: sodium, potassium, calcium, and magnesium as cations; and chlorides and bicarbonates as anions, with the bicarbonates serving above all as a buffer agent (and below the term "bicarbonate" is used as being generic over all of the bicarbonates in question). Instead of having this particular buffer agent, the second liquid could contain precursors of the buffer agent, such as acetate or acetate plus lactate, which precursors are transformed into bicarbonate by the human body. If the second liquid contains bicarbonates, a sufficient quantity of acetic acid is added thereto to prevent the calcium and magnesium ions causing the bicarbonate ions to precipitate. The concentration of sodium ions and chloride ions in the second liquid is identical to that in the first liquid so that no significant diffusion of these ions takes place through the membrane 4.

With these two liquids, diffusion transfers through the exchanger take place essentially from the second liquid to the first liquid.

EXAMPLE 2

The first liquid is a solution of chlorides of sodium, calcium, and magnesium. The second liquid contains the main electrolytes of blood, including bicarbonate as a buffer agent, but not including calcium and magnesium ions, thereby avoiding the problem of undesirable precipitation of bicarbonate ions due to calcium ions and magnesium ions being present in the second liquid. Since the concentration of calcium and magnesium ions in the second liquid is zero, these ions diffuse through the exchanger from the first liquid into the second. In order to obtain a desired concentration of calcium and magnesium ions in the substitution liquid, it is therefore necessary to choose a first liquid in which the concentration of calcium and magnesium ions is greater than the desired concentration in order to compensate for losses by diffusion.

EXAMPLE 3

The first liquid is a solution of sodium bicarbonate. The second liquid contains the main electrolytes of blood other than bicarbonate. In similar manner to that observed in Example 2, since the concentration of bicarbonate ions in the second liquid is zero, these ions diffuse in the exchanger from the first liquid into the second. In order to obtain a desired concentration of bicarbonate in the substitution liquid, it is therefore necessary to select a first liquid in which the bicarbonate concentration is greater than the desired concentration in order to compensate for diffusion losses.

The above-described apparatus for preparing a substitution liquid operates as follows. Once the first and second liquids have been respectively selected and prepared, the supplies 7 and 17 and the exchanger 1 are installed on a support (not shown) of the apparatus. Similarly, the first and second circuits are installed connecting the upstream and downstream portions 5, 16, and 6, 27 of these circuits to the exchanger 1 and to the supplies 7 and 17. Before connecting the ducts 8 of the first circuit to the first liquid supply 7, the first circuit and the first chamber 2 of the exchanger 1 to which it is connected are washed with a liquid that is sterile and pyrogen-free, after which the first circuit and the chamber 2 are initially filled (i.e. are "primed") with the same liquid. Advantageously, the liquid used for washing and for priming is the first liquid.

Once the desired flow rate QL of substitution liquid has been entered into the control unit 25, it causes the pump 10 to operate in such a manner as to ensure that the flow rate through the pump 10 is substantially equal to QL. If the pump 20 is to be servo-controlled to the pump 10, then the control unit 25 also controls rotation of the pump 20 so that the exchange rates through the exchanger are substantially constant. Once the initial fill of liquid in the first circuit has been completely expelled by the first liquid, and once the second liquid has completely filled the second circuit and has begun to flow out through the duct 21, then the liquid which leaves via the cannula connected to the end of the first circuit is the desired substiution liquid. The cannula can then be inserted into a vein of the patient 12 and injection may begin. On the basis of the information provided by the flow meter 11, which the control unit 25 compares with the desired flow rate QL for the substitution liquid, the rate of rotation of the pump 10 is adjusted so that the real flow rate is equal to the desired flow rate. The control unit 25 also controls operation of the heater unit 23 and adjusts the amount of heating provided thereby as a function of QL.

Figure 2:
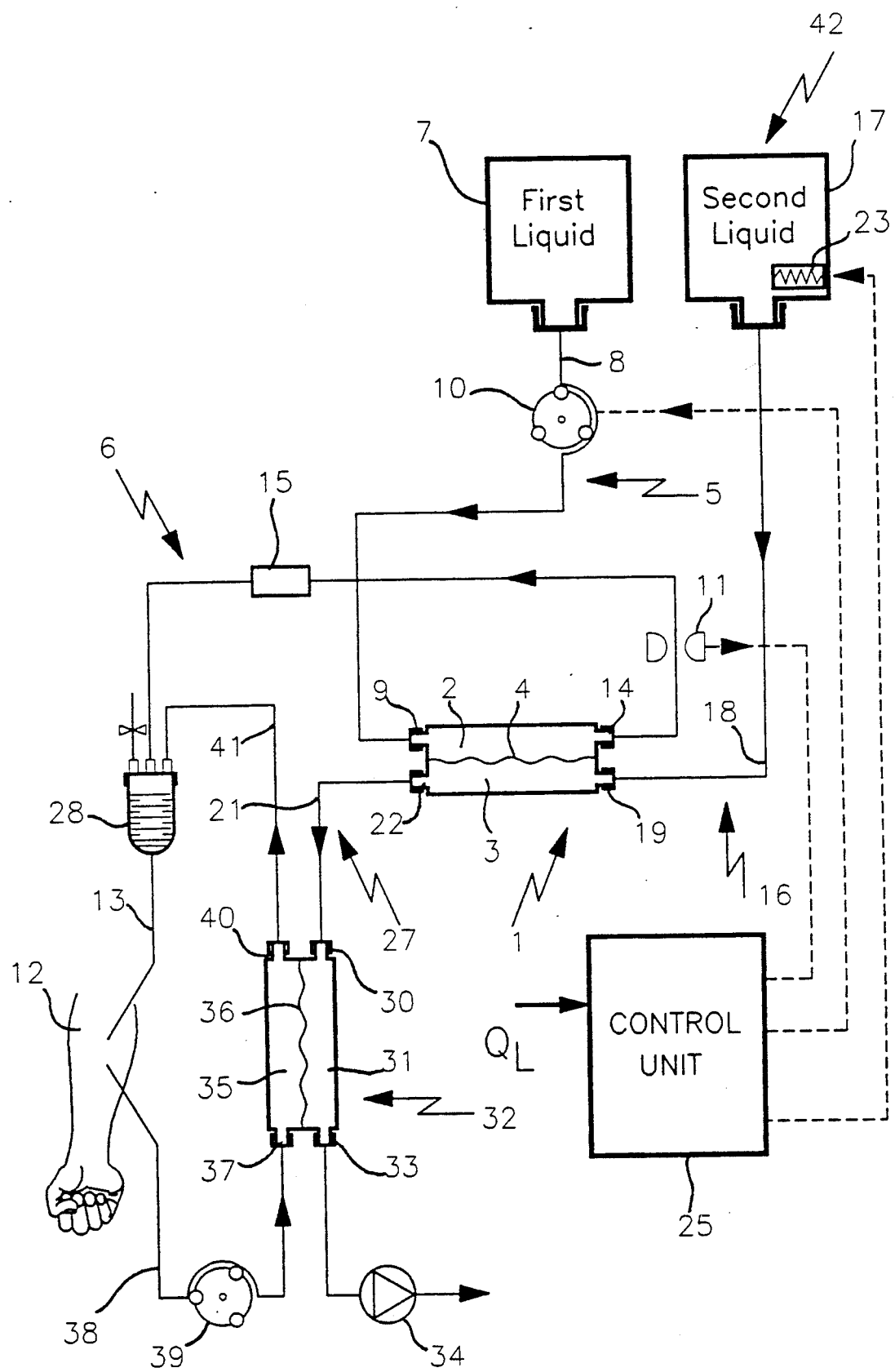
FIG. 2 is a diagram showing the combination of hemodiafiltration apparatus together with apparatus of the invention for preparing substitution liquid.

FIG. 2 shows a second apparatus for preparing substitution liquid in association with hemodiafiltration apparatus. In this figure, the reference numerals used in FIG. 1 are used again to designate corresponding items of this second apparatus of the invention.

This apparatus for preparing substitution liquid differs from the preceding apparatus essentially in that the downstream portion 27 of the second circuit, instead of having its free end opening out into a wastewater disposal system, is connected to an inlet 30 of a first chamber 31 of a dialyzer 32 whose outlet 33 is connected to a conventional dialysis circuit (shown in part) which includes, in particular, a pump 34 for circulating the dialysis liquid. In the hemodiafiltration apparatus shown in FIG. 2, it is thus the liquid coming from the second liquid supply 17 which is used as the dialysis liquid after it has passed through the exchanger 1.

The second chamber 35 of the dialyzer 32 which is separated from the first chamber 31 by a semipermeable membrane 36 has an inlet 37 connected to an artery line 38 on which a blood circulation pump 39 is disposed, and an outlet 40 connected to a vein line 41 opening out in the degassing chamber 28.

In this second embodiment of apparatus for preparing substitution liquid as shown in FIG. 2, the second circuit does not include a pump for the second liquid, with the second liquid being caused to flow by the pump 34 of the hemodiafiltration apparatus.

The pumps 10 and 34 operate independently from each other. An advantageous characteristic of this apparatus lies in the fact that, given the flow rates generally used for the dialysis liquid and for the substitution liquid, there exist exchangers having characteristics such that any variation in the substitution liquid flow rate, even over a relatively wide range, does not have any influence on the ion transfer rate through the exchanger for a given flow rate of dialysis liquid.

In other words, starting from liquids having respective determined compositions upstream from the exchanger 1, and operating at a given dialysis liquid flow rate, the respective compositions of the liquids downstream from the exchanger 1 (dialysis liquid, substitution liquid) do not change significantly regardless of the flow rate selected for the substitution liquid over a fairly large given range of flow rates. For example, in an exchanger fitted with a membrane having an area of about 0,5 m², of the type known under the trade name Cuprophan, and operating at a dialysis liquid flow rate substantially equal to 500 ml/min, substantially 100% equilibrium occurs between the liquids in the exchanger 1 providing the flow rate of the substitution liquid lies in a range running from about 0 to about 50 ml/min.

Compared with the apparatus described with reference to FIG. 1, this apparatus also has a variant in which the connections of the upstream and downstream portions 5, 16 and 6, 27 of the first and second circuits with the exchanger 1 are crossed, so that the liquids flow in counterflow through the chambers 2 and 3 of the exchanger 1, thereby enhancing ion transfers through the membrane 3. Although such a counterflow disposition theoretically increases the risk of backfiltering compared with the same-direction parallel-flow disposition shown in FIG. 1, other things remaining equal, the actual risk in the present case is low insofar as firstly the respective pressures in the blood circuit and in the dialysis circuit of a hemodiafiltration circuit are conventionally adjusted so that positive transmembrane pressure exists between the dialyzer chamber containing blood and the dialyzer chamber containing dialysis liquid, and secondly in the installation shown in FIG. 2, the pressure in the blood circuit and the pressure in the substitution liquid circuit are substantially equal, said circuit being in communication via the degassing chamber 28 so that here again, when the hemodiafiltration apparatus is in operation, positive transmembrane pressure exists between the chamber 2 containing the substitution liquid and the chamber 3 containing the dialysis liquid in the exchanger 1.

The compositions of the first and second liquids used to prepare the substitution liquid in this second apparatus are no different from those described above. In contrast, the concentrations of the electrolytes respectively contained therein are adjusted so that the liquid leaving the second chamber 3 of the exchanger 1 has the characteristics of a dialysis liquid. This adjustment of concentrations as a function of the transfer rate through the exchanger 1 for the purpose of producing both a substitution liquid and a dialysis liquid of determined composition and electrolyte concentration is achieved by applying conventional laws for ion transfers through the semipermeable membranes.

In this second apparatus for preparing a substitution liquid, the second liquid is advantageously prepared continuously and is heated in a dialysis liquid generator 42 which includes the heater member 23 and which forms a portion of the hemodiafiltration apparatus with which the apparatus of the invention is associated. In order to ensure that the liquid injected into the patient 12 and that the second liquid downstream from the exchanger 1 which is used as the dialysis liquid are both at about 37° C., the heater member 23 raises the second liquid to a temperature higher than 27° C. in order to enable it to heat the first liquid in the exchanger 1 and to compensate for heat losses that take place in the first and second circuits.

The operation of this apparatus does not differ significantly from that described above with reference to the apparatus shown in FIG. 1.

It should be observed that once the first liquid circuit is connected to the supply 7 and once this circuit has been connected to the blood circuit (ducts 38, 41, and chamber 35 of dialyzer 32) via the degassing chamber 28, the first liquid may be used as a washing liquid and as a priming liquid both for the first liquid circuit and for the blood circuit.

The present invention is not limited to the embodiments described above, and it may be subjected to modifications and to variants.

What is claimed is:

1. A method for preparing a substitution using an exchanger divided into two compartments by a semipermeable membrane, the method comprising the steps of:

flowing a sterile and pyrogen-free first liquid through the first compartment; and flowing a second liquid through the second compartment to vary an electrolyte composition of the first liquid, thereby transforming the first liquid into a substitution liquid for injection into a vascular system of a patient, each of the first and second liquids containing at least one electrolyte of blood and said at least one electrolyte of blood including at least one agent chosen from the group consisting of buffer agents and precursors of buffer agents, at least some of the electrolytes being present in the first and second liquids in different concentrations prior to the steps of flowing the first and second liquids through the first and second compartments, respectively.

2. A method according to claim 1, further comprising the step of heating one of the first and second liquids upstream of the exchanger so that downstream of the exchanger the first liquid is at approximately human body temperature.

3. A method according to claim 1, further comprising the step of using the second liquid downstream of the exchanger as a dialysis liquid.

4. A method according to claim 1, further comprising the step of adjusting flow rates of the first and second liquids through the exchanger so that a flow rate ratio of the first and second liquids is substantially constant.

5. A method according to claim 1, further comprising the step of adjusting the flow rate of the second liquid as a function of a flow rate of the first liquid.

6. A method according to claim 1, wherein the first and second liquids flow through the exchanger in a counterflow disposition.

7. A method according to claim 1, wherein the first and second liquids flow through the exchanger in a same-direction parallel-flow disposition.

8. A method according to claim 1, further comprising the step of maintaining a positive transmembrane pressure between a face of the membrane in contact with the first liquid and a face of the membrane in contact with the second liquid.

9. A method according to claim 1, further comprising the step of using the first liquid as a washing liquid and as a priming liquid for a first circuit connecting a source of the first liquid to a patient.

10. A method according to claim 1, wherein the first liquid is a solution of sodium chloride.

11. A method according to claim 1, wherein the first liquid is a solution of sodium, calcium, and magnesium chlorides.

12. A method according to claim 1, wherein the first liquid contains bicarbonate and is substantially magnesium-free, and the second liquid contains calcium and magnesium, and is substantially bicarbonate-free.

13. A method as set forth in claim 1 wherein the step of flowing the second liquid through the second compartment serves to enrich the first liquid in the first compartment with blood electrolytes.

14. An apparatus for preparing a substitution liquid, the apparatus comprising:
 a first liquid source having a first liquid disposed therein, the first liquid being sterile and pyrogen-free; and
 means for transforming the first liquid into a substitution liquid for injection into a vascular system of a patient, the transforming means including
  (a) a second liquid source having a second liquid disposed therein, the second liquid having an electrolyte composition that varies from an electrolyte composition of the first liquid;
  (b) an exchanger having first and second compartments separated by a semipermeable membrane, each of the first and second compartments having an inlet and an outlet;
  (c) means for connecting the first liquid source with the inlet of the first compartment; and
  (d) means for connecting the second liquid source with the inlet of the second compartment;
 wherein each of the first and second liquids contain at least one electrolyte of blood, and said at least one electrolyte of blood includes at least one agent chosen from the group consisting of buffer agents and precursors of buffer agents.

15. An apparatus according to claim 14, wherein the source of the second liquid is a dialysis liquid generator.

16. An apparatus according to claim 14, further including heater means for heating one of the first and second liquids upstream of the exchanger.

17. An apparatus according to claim 14, further including a first pump for causing the first liquid to flow, and a second pump for causing the second liquid to flow.

18. An apparatus according to claim 17, further including control means for adjusting a flow rate of the second pump as a function of a flow rate of the first pump.

19. An apparatus according to claim 18, further including a flow meter for measuring a flow rate of the first liquid, the control means also for adjusting the flow rate of the first pump as a function of a comparison between measurements provided by the flow meter and at least one reference value.

20. An apparatus according to claim 14, wherein the outlet of the first compartment of the exchanger is connected to a bacteria filter.

21. The apparatus as set forth in claim 14 further including a dialyzer, the outlet of said second compartment being connected to the dialyzer.

* * * * *

UNITED STATES PATENT AND TRADEMARK OFFICE
CERTIFICATE OF CORRECTION

PATENT NO. : 5,178,763
DATED : January 12, 1993
INVENTOR(S) : March DeLaunay

It is certified that error appears in the above-indentified patent and that said Letters Patent is hereby corrected as shown below:

Claim 1, Column 8, line 61, after "substitution" insert —liquid—;

Column 9, line 4, delete "said";

Claim 14, Column 10, line 24, delete "said".

Signed and Sealed this

Twenty-ninth Day of March, 1994

Attest:

BRUCE LEHMAN

*Attesting Officer*     *Commissioner of Patents and Trademarks*